United States Patent [19]

Jefson

[11] Patent Number: 5,235,054
[45] Date of Patent: Aug. 10, 1993

[54] 3-CARBOXALDEHYDE SUBSTITUTED QUINOLINES AND NAPHTHYRIDINES

[75] Inventor: Martin R. Jefson, Stonington, Conn.

[73] Assignee: Pfizer Inc., New York, N.Y.

[21] Appl. No.: 914,188

[22] Filed: Jul. 15, 1992

[51] Int. Cl.$^5$ .................................... C67D 215/16
[52] U.S. Cl. .................................... 546/156
[58] Field of Search .................... 546/156; 514/312

[56] References Cited

U.S. PATENT DOCUMENTS

| | | | |
|---|---|---|---|
| 4,775,668 | 10/1988 | Jefson et al. | 514/183 |
| 4,861,779 | 8/1989 | Jefson et al. | 514/249 |
| 5,091,383 | 2/1992 | Jefson et al. | 514/214 |

FOREIGN PATENT DOCUMENTS

| | | | |
|---|---|---|---|
| 0070767 | 1/1983 | European Pat. Off. | 546/156 |
| 0364943 | 4/1990 | European Pat. Off. | |

OTHER PUBLICATIONS

Kondo et al., J. of Med. Chem., 31, 221-225 (1988).
Chu et al., Drugs Exptl. Clin. Res., XVI (9), 435-443 (1990).

*Primary Examiner*—Marianne M. Cintins
*Assistant Examiner*—Michael B. Hydorn
*Attorney, Agent, or Firm*—Peter C. Richardson; Paul H. Ginsburg; Gezina Holtrust

[57] ABSTRACT

The following 3-carboxaldehyde quinolines and naphthyridines have antibacterial activity

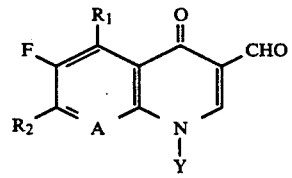

wherein A, Y, R, and $R_2$ are as defined herein. These compounds are particularly suitable for administration by injection. A specific example of such compound is 1-cyclopropyl-6-fluoro-7-[(1S,4S)-5-methyl-2,5-diazabicyclo[2.2.1]hept-2-yl]-4-oxo-1,4-dihydroquinoline-3-carboxaldehyde.

5 Claims, No Drawings

3-CARBOXALDEHYDE SUBSTITUTED QUINOLINES AND NAPHTHYRIDINES

BACKGROUND OF THE INVENTION

This invention relates to quinoline and naphthyridine prodrugs having a 3-carboxaldehyde group, to antibacterial compositions containing said prodrugs and to a method of treating bacterial infections by administering said prodrugs.

Antibacterial compounds derived from quinolines and naphthyridines are described in the prior art. U.S. Pat. No. 4,861,779, which is incorporated herein by reference, discloses such compounds having a 3-carboxylic acid group.

European patent publication 365 943 refers to antibacterial quinoline prodrugs which have a carboxaldehyde group at the three position. Kondo et al., J. of Medicinal Chem., 31,221 (1988) refers to oral administration of 3-carboxaldehyde quinolines which are rapidly metabolized into the corresponding 3-carboxyl quinolines and result in higher serum levels than those of the corresponding 3-carboxy quinoline. Chu et al., Drugs Exptl. Clin. Res., XVI(9), 435 (1990) refers to the 3-carboxaldehyde prodrug of tosulfloxacin having improved water solubility when compared to tosulloxacin itself allowing for the development of intravenous formulations of the prodrug. These publications do not refer to tissue damage encountered with intramuscular injection of 3-carboxy quinolines.

SUMMARY OF THE INVENTION

In accordance with the invention, compounds are provided having the formula

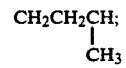

wherein A is CH, CF, or N; Y is ethyl, cyclopropyl, 4-fluorophenyl, or 2,4-difluorophenyl; or A and Y when taken together are

O—CH$_2$—CH—C,
  |
  CH$_3$

CH$_2$—CH$_2$—CH—C,
  |
  CH$_3$ or

O—CH$_2$—N—C;
  |
  CH$_3$

R$_1$ is hydrogen or methyl, and R$_2$ is hydrogen, 5-methyl-2,5-diazabicyclo[2.2.1]hept-2-yl, 8-methyl-3,8-diazabicyclo[3.2.1]oct-3-yl, 1,4-diazabicyclo[3.2.2]non-4-yl, with the proviso that when R$_2$ is hydrogen, then A and Y are taken together to form

CH$_2$CH$_2$CH;
  |
  CH$_3$ and the pharmaceutically acceptable acid addition salts thereof when R$_2$ is other than hydrogen.

Specific compounds of the invention are the 3-carboxaldehyde derivatives of danofloxacin, binfloxacin, and flumequine.

The invention includes antibacterial compositions comprising a compound of the formula I as defined above in an amount sufficient for the treatment of bacterial infections, and a pharmaceutically acceptable carrier.

The invention further includes a method of treating a host affected by a bacterial infection by administering to said host an antibacterially effective amount of a compound of the formula I as defined above. The invention is particular of use for treatment by injection. It has been found according to the invention that the compounds of formula I are advantageous over the corresponding 3-carboxylic acids in view of reduction in tissue damage at the injection site. The invention also includes a method for the intramuscular injection of a host with the 3-carboxaldehyde prodrug of difloxacin, enrofloxacin, lomefloxacin, norfloxacin, sarafloxacin or temafloxacin to reduce the tissue damage encountered with the corresponding 3-carboxylic acids of these antibacterial compounds.

DETAILED DESCRIPTION OF THE INVENTION

The compounds of formula I may be prepared as depicted in the following Reaction Scheme.

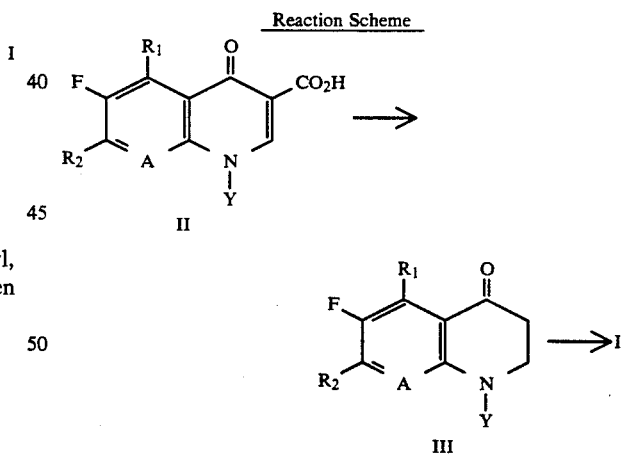

The carboxylic acids of formula II wherein A, Y, R$_1$ and R$_2$ are as defined with reference to formula I are reacted with a suitable reducing agent followed by acidification to form the compound of formula III wherein A, Y, R$_1$ and R$_2$ are as defined with reference to formula I. Suitable reducing agents include borohydrides, e.g. sodiumborohydride or sodiumcyanoborohydride. The reaction is generally carried out in a solvent which is inert under the reaction conditions. Suitable solvents include water, lower alcohols such as methanol and ethanol, and mixtures thereof. The reaction temperature generally ranges from about 0° C. to about room temperature.

The acidification is with a concentrated acid resulting in liberation of carbon dioxide from the reaction mixture. Suitable acids include mineral acids such as hydrochloric acid and sulfuric acid, and sulfonic acids such as methanesulfonic acid. The reaction mixture is conveniently heated such that the reaction proceeds under gentle reflux of the solvent used.

The compound of formula III is converted to the compound of formula I in a two step procedure. The first step entails formation of a ketone enolate intermediate by reaction with a sodium alkoxide such as sodium methoxide followed by formylation with a lower alkyl formate such as ethylformate, in the presence of an ethereal solvent such as ether, tetrahydrofurane, dioxane or dimethyl formamide. This reaction is carried out at about room temperature, although higher temperatures may be used to accelerate the reaction. In the second step, the formed ketoaldehyde is oxidized with manganese dioxide in a lower alkanol solvent such as ethanol at about room temperature or higher temperatures for faster reaction.

The 3-carboxaldehyde prodrugs of difloxacin, enrofloxacin, lomefloxacin, norfloxacin, sarafloxacin and temafloxacin are prepared by similar methods as described above. These prodrugs and those of formula I are conveniently referred to herein as "prodrugs of the invention."

Whenever reference is made herein to "lower" alkyl, alkoxy, or alkanol, a carbon atom range of one to six is meant.

The pharmaceutically acceptable acid addition salts of the prodrugs of the invention include salts with pharmaceutically acceptable acids such as acetic, lactic, succinic, maleic, tartaric, citric, gluconic, ascorbic, benzoic, methanesulfonic, cinnamic, fumaric, phosphoric, hydrochloric, hydrobromic, hydroiodic, sulfam, pivalic, stearic and sulfonic acid. These salts are prepared in a conventional manner by treating a solution or suspension of the compound of formula I, wherein $R_2$ is other than hydrogen, with about one chemical equivalent of a pharmaceutically acceptable acid.

Although the prodrugs of the invention may be administered orally, they are advantageously injected in view of the reduced tissue damage at the injection site when compared with the corresponding carboxylic acids. It has been found that bioavailability and antibacterial activity in vivo of the present prodrugs are comparable to those of the corresponding carboxylic acids. The advantage of the present prodrugs is therefore mainly noticeable on administration by injection into the host.

The prodrugs of the invention are conveniently injected into the host such as cattle by intramuscular, subcutaneous or intravenous injection. For injection, sterile aqueous solutions of the active compound or solutions in sesame oil, peanut oil or aqueous propylene glycol can be prepared. The aqueous solutions should be suitably buffered, if necessary, and the liquid diluent rendered isotonic with sufficient saline or glucose, as known to those skilled in the art.

The weight ratio of prodrug to carrier will generally range from 1:6 to 2:1, preferably from 1:4 to 1:1. However, the ratio chosen will depend on factors such as the solubility of the prodrug, the dosage and the precise route of administration.

The dosage of the prodrug of the invention may vary according to administration methods, age and weight of the host, severity of the injection and the like and usually ranges from 1 to 500 mg/day.

The following example illustrates the invention.

EXAMPLE

A.

1-Cyclopropyl-6-fluoro-7-[(1S,4S)-5-methyl-2,5-diazabicyclo[2.2.1.]hept-2-yl]-4-oxo-1,2,3,4-tetrahydroquinoline To a slurry danofloxacin mesylate (25.9 g, 57.2 mmoles) in 500 ml of methanol at 0° C. was added sodium borohydride (10.9 g, 286 mmoles) in small portions over 15 minutes. The resulting bright yellow slurry was allowed to warm to room temperature and stir for 20 hours. At this time the reaction mixture was chilled to 0° C. and another portion of sodium borohydride (10.9 g, 286 mmoles) was added in the manner described above. The reaction mixture was warmed to room temperature and allowed to stir for an additional 28 hours. At this time 50 ml of concentrated hydrogen chloride was added and the reaction mixture was heated in an oil bath to 60° C. for 90 minutes, then cooled to room temperature, and poured carefully into 800 ml of stirring saturated sodium bicarbonate. The methanol was then removed under reduced pressure and the resulting aqueous solution was extracted three times with 500 ml of ethyl acetate. The combined ethyl acetate extracts were washed once with water, dried over magnesium sulfate and evaporated to dryness. The resulting brown residue was purified by column chromatography (500 g, silicon dioxide, 19/1 of chloroform methanol eluant) to give the title compound (9.4 g, 52% yield) as a waxy yellow solid.

B. Cyclopropyl-6-fluoro-1,4-dihydro-7-[(1S, 4S)-5-methyl-2,5-diazabicyclo-[2.2.1]hept-2-yl]-4-oxoquinoline-3-carboxaldehyde To a solution of the compound of Step A (9.4 g, 29.8 mmoles) in 300 ml of dry ethyl ether at room temperature was added sodium methoxide (6.45 g, 119 mmoles) in one portion. The resulting slurry was stirred for 15 minutes at which time ethyl formate (9.63 ml, 119 mmoles) was added by syringe. The reaction mixture was then allowed to stir at room temperature for 40 hours. At this time the resulting yellow-brown slurry was poured slowly into 800 ml of 10% glacial acetic acid in water. The pH of this aqueous mixture was adjusted to 6.5 with sodium bicarbonate and the solution was then extracted five times with 300 ml of chloroform. The combined chloroform extracts were washed twice with water, dried over magnesium sulfate and evaporated to a yellow-orange residue. The residue was taken up in 500 ml methanol and manganese dioxide (10.4 g, 120 mmoles) was added to it. The resulting slurry was stirred at room temperature for 18 hours at which time it was warmed to 60° C. and filtered. The filter cake was washed twice with 100 ml methanol and the combined filtrates were concentrated to 100 ml in volume and cooled in an ice-water bath. The resulting precipitate was filtered, washed three times with ethyl ether and dried under vacuum to give the title compound (6.9 g, 68% yield) as a cream colored solid (m.p. 274°-275° C.). $^1$H NMR (300 MHz, CDCl$_3$): 10.34 (1H,s), 8.30 (1H,s), 7.94 (1H,d,J=14 Hz), 6.86 (1H, d, J=8 Hz), 4.62 (1H, br s), 3.51-3.63 (3H, m), 3.40 (1H, m), 2.97 (1H, br d, J=10 Hz), 2.89 (1H, br d, J=10 Hz), 2.46 (3H, s), 2.06 (1H, br d, J=11 Hz), 1.94 (1H, br d, J=11 Hz), 1.21-1.36 (2H, m), 1.08-1.20 (2H, m).

C.
1-Cyclopropyl-6-fluoro-1,4-dihydro-7-[1S,4S)-5-methyl-2,5-diazabicyclo[2.2.1]hept-2-yl]-4-oxo-quinoline-3-carboxaldehyde, methanesulfonate To a slurry of the compound of step B (10.2 g, 30 mmoles) in 100 ml ethanol at room temperature was added methanesulfonic acid (2.04 ml, 31.5 mmoles). The resulting thick slurry was allowed to stir at room temperature for 1 hour. The mixture was then cooled to 0° C. in an ice-water bath and filtered. The solid was washed twice with 50 ml of cold ethanol and dried at 60° C. in a vacuum oven overnight to give the title compound (10.3 g, 78.5% yield) as a cream colored solid (m.p. 272°-273° C.)

I claim:

1. 1-Cyclopropyl-6-fluoro-7-[(1S,4S)-5-methyl-2,5-diazabicyclo[2.2.1]hept-2-yl]-4-oxo-1,4-dihydroquinoline-3-carboxaldehyde, or the pharmaceutically acceptable acid addition salts thereof.

2. A compound according to claim 1 wherein said pharmaceutically acceptable addition salt is the monomethanesulfonate salt.

3. An antibacterial composition which comprises 1-cyclopropyl-6-fluoro-7-[(1S, 4S)-5-methyl-2,5-diazabicyclo[2.2.1]hept-2-yl]-4-oxo-1,4-dihydroquinoline-3-carboxaldehyde or a pharmaceutically acceptable acid addition salt thereof in an amount sufficient for the treatment of bacterial infection, and a pharmaceutically acceptable carrier.

4. A composition according to claim 3 wherein said pharmaceutically acceptable acid salt is the monomethanesulfonate salt.

5. A composition according to claim 4 wherein said pharmaceutically acceptable carrier is an injectable solution.

* * * * *